US005962463A

United States Patent [19]
Nitsch et al.

[11] Patent Number: 5,962,463
[45] Date of Patent: Oct. 5, 1999

[54] METHODS OF STIMULATING NON-AMYLOIDOGENIC PROCESSING OF THE AMYLOID PRECURSOR PROTEIN

[75] Inventors: Roger M. Nitsch; Richard J. Wurtman, both of Boston, Mass.

[73] Assignee: Massachusetts Institute Of Technology, Cambridge, Mass.

[21] Appl. No.: 08/789,336

[22] Filed: Jan. 27, 1997

Related U.S. Application Data

[63] Continuation of application No. 08/337,993, Nov. 10, 1994, abandoned, which is a continuation-in-part of application No. 08/228,078, Apr. 15, 1994, which is a continuation-in-part of application No. 07/959,253, Oct. 9, 1992, abandoned.

[51] Int. Cl.$^6$ ........................ A61K 31/44; A61K 31/405; A61K 31/40; A61K 31/135; A61K 31/13
[52] U.S. Cl. ........................ 514/284; 514/415; 514/428; 514/641; 514/649; 514/651; 514/662
[58] Field of Search ..................................... 514/284, 415, 514/428, 641, 649, 651, 662

[56] References Cited

U.S. PATENT DOCUMENTS

| | | | |
|---|---|---|---|
| 4,604,397 | 8/1986 | Hutchison | 514/219 |
| 5,470,846 | 11/1995 | Sandyk | 514/159 |

FOREIGN PATENT DOCUMENTS 0 457 295 A2  11/1991  European Pat. Off. .

OTHER PUBLICATIONS

Nitsch, R. M., et al., "Release of Alzheimer Amyloid Precursor Derivatives Stimulated by Activation of Muscarinic Acetylcholine Receptors," *Science*, 258:304–307 (1992).

Sandmann, J., et al., "Coupling of Transfected Muscarinic Acetylcholine Receptor Subtypes to Phospholipase D," *J. Biol. Chem.*, 266(10):6031–6034 (1991).

Peralta, E. G., et al., "Differential Regulation of PI Hydrolysis and Adenylyl Cyclase by Muscarinic Receptor Subtypes," *Nature*, 334:434–437 (1988).

Weidemann, A., et al., "Identification, Biogenesis, and Localization of Precursors of Alzheimer's Disease A4 Amyloid Protein," *Cell*, 57:115–126 (1989).

Golde, T. E., et al., "Processing of the Amyloid Protein Precursor to Potentially Amyloidogenic Derivatives," *Science*, 255:728–730 (1992).

Estus, S., et al., "Potentially Amyloidogenic, Carboxyl–Terminal Derivatives of the Amyloid Protein Precursor," *Science*, 255:726–728 (1992).

Samanin, R. and Garattini, S., "The Pharmacology of Serotoninergic Drugs Affecting Appetite," *Nutrition and the Brain*, 8:162–193 (1990).

Fleisher and Campbell, *The Lancet*, 1969:1306 (1969).

Saitoh, T., et al., "Aberrant Protein Kinase C Cascades in Alzheimer's Disease," *Adv. Exp. Med. Biol.* 265:301–310 (1990).

Caporaso, G. L., et al., "Protein Phosphorylation Regulates Secretion of Alzheimer β/A4 Amyloid Precursor Protein," *Proc. Natl. Acad. Sci. USA*, 89:3055–3059 (1992).

Chauhan, A., et al., "Action of Amyloid Beta–Protein on Protein Kinase C Activity," *Life Sciences*, 49:1555–1562 (1991).

Gandy, S., et al., "Phosphorylation of Alzheimer Disease Amyloid Precursor Peptide by Protein Kinase C and $Ca^{2+}$/calmodulin Dependent Protein Kinase II," *Proc. Natl. Acad. Sci. USA*, 85:6218–6221 (1988).

Kiefer–Day, J. S., and El–Fakahany, E. E., "Muscarinic Receptor Function and Acetylcholinesterase Activity After Chronic Administration of Tacrine to Mice at Therapeutic Drug Concentrations," *Pharmacology*, 44:71–80 (1992).

Small, D. H., et al., "A Protease Activity Associated with Acetylcholinesterase Releases the Membrane–Bound Form of the Amyloid Protein Precursor of Alzheimer's Disease," *Biochemistry*, 30:10795–10799 (1991).

Suzuki, T., et al., "Phosphorylation of Alzheimer Amyloid Precursor Protein by Protein Kinase C," *Neuroscience*, 48(4):755–761 (1992).

Shimoham, S., et al., "Acetylcholine Receptors in Alzheimer–type Dementia," Recent Research on Neurotransmitter Receptors Proceedings of the 2nd Workshop on Neurotransmitters & Diseases Tokyo, Jun. 15, 1985. Yoshida, H. (ed.), *Experpta Medica*, 1986. (*Excerpta Medica*, Int'l Congress Series No. 710) pp. 2–12.

Krogsgaard–Larsen, P., "Alzheimer's Disease: Acetylcholine and Glutamic Acid Receptors as Therapeutic Targets," *Act. Chim. Ther.*, 17:161–73 (1990).

The Merck Index; Eleventh Edition, No. 3920, 1989.

*Primary Examiner*—Theodore J. Criares
*Attorney, Agent, or Firm*—Lowe, Price, LeBlanc & Becker

[57] ABSTRACT

Stimulating non-amyloidogenic processing by the activation of cell surface serotonin receptors linked to phospholipase and protein kinase C is described. Activation of the cell surface serotonin receptors is accomplished by contacting the cell with an agent which is a serotonin agonist or which increases the intrasynaptic concentration of serotonin. Also described is the activation of cell surface serotonin receptors by dexnorfenfluramine. Agents which cause the activation of cell surface serotonin receptors can be administered to an individual to stimulate non-amyloidogenic processing in the brain of the individual, thereby inhibiting the deposition of amyloid in the brain of the individual.

29 Claims, 4 Drawing Sheets

TRANSFECTED 5-HT$_{1C}$ RECEPTORS STIMULATE APPs SECRETION IN NIH 3T3 CELLS

Dexnorfenfluramine stimulates APP$^s$ release from 3T3 fibroblasts expressing 5-HT$_{1c}$ receptor cDNA Data are means ± S.E.M., n=3

Dexnorfenfluramine stimulates PI-turnover in 3T3 fibroblasts expressing 5-HT$_{1c}$ receptor cDNA Data are means ± S.D. (when larger than symbol), n=3

METHODS OF STIMULATING NON-AMYLOIDOGENIC PROCESSING OF THE AMYLOID PRECURSOR PROTEIN

RELATED APPLICATIONS

This application is a continuation of application Ser. No. 08/337,993 filed Nov. 10, 1994, now abandoned, which is a Continuation-in-Part (CIP) of U.S. Ser. No. 08/228,078, filed Apr. 15, 1994, pending which is a Continuation-in-Part of U.S. Ser. No. 07/959,253, filed Oct. 9, 1992, now abandoned. The entire teachings of both cited applications expressly are incorporated herein by reference.

Funding

Work described herein was supported in whole or in part by Government funding under Grant No. MN-28783 awarded by NIMH. The government has rights in this invention.

BACKGROUND

Alzheimer's disease (AD) is a chronic progressive neurodegenerative disease. Clinically, it is characterized by progressive deficits in memory and other cognitive functions that occur in the face of an otherwise normal neurological examination. Postmortem examination reveals a variety of typical AD brain lesions, including deposition of amyloid plaques, formation of neurofibrillary tangles, and neuronal degeneration.

The amyloid deposits characteristic of AD pathology consist of aggregates of a 39–42 amino acid peptide termed β/A4 (G. G. Glenner and C. W. Wong, *Biochem. Biophys. Res. Comm.*, 120: 885 (1984); C. L. Masters, et al., *Proc. Natl. Acad. Sci. USA,* 82: 4245 (1985); D. J. Selkoe, et al., *J. Neurochem.,* 46: 1820 (1986)), which is an abnormal cleavage product of a larger amyloid precursor protein (APP) (J. membrane glycoprotein, existing as several distinct forms derived from alternative mRNA splicing (R. E. Tanzi, et al., *Nature,* 331: 528–530 (1988); P. Ponte, et al., *Nature,* 331: 525 (1988); N. Kitaguchi, et al., *Nature.,* 331: 530 (1988)). Water-soluble APP fragments lacking the COOH terminus (APP$^s$) have been detected in conditioned cell culture media and in human cerebrospinal fluid (A. Weidemann, et al., *Cell,*57: 115, (1989), M. R. Palmert, et al., *Proc. Natl. Acad. Sci. USA,* 86: 6338 (1989)), indicating that APP$^s$ is a secretory protein. Normal secretion of water-soluble NH$_2$-terminal APP fragments involves cleavage of full-length APP at an extracellular site located close to the transmembrane domain, and within the β/A4 domain (T. Oltersdorf, et al., *Nature,* 341: 144 (1989); F. S. Esch, et al., *Science,* 248: 1122 (1990); S.S. Sisodia, et al., *Science,* 248: 492 (1990); J. P. Anderson, et al., *Neurosci. Lett.,* 128: 126 (1991); R. Wang, et al., *J. Biol. Chem.,* 262: 16960 (1991)). This cleavage event presumably precludes the formation of amyloidogenic APP fragments. It is also possible that APP is processed by an internal lysosomal pathway (C. Haass, A. Y. Hung, D. J. Selkoe, *J. Neurosci.,* 11: 3783 (1991); C. Haass, E. H. Koo, A. Mellon, A. Y. Hung, D. J. Selkoe, *Nature,* 356: 500 (1992)) that may generate amyloidogenic cleavage products (S. Estus, et al., *Science,* 255: 726 (1992); T. E. Golde, S. Estus, L. H. Younkin, D. J. Selkoe, S. G. Younkin, *Science,* 255: 728 (1992)). It is therefore likely that aberrations of APP processing pathways contribute to amyloid formation. The mechanisms regulating cellular APP processing, however, are unknown.

SUMMARY OF THE INVENTION

This invention is based on the results of an assessment of control of APP processing in cells. As described herein, it has been discovered that cell-surface neurotrarLsmitter receptors linked to phospholipase C and a protein kinase, in particular serotonin-1C (5HT$_{1C}$) receptors and serotonin-2 (5HT$_2$) receptors, regulate APP processing. It has been shown that cellular release of the water soluble NH$_2$-terminal cleavage product of APP (APP$^s$) is controlled by cell-surface neurotransmitter receptor activity (i.e., APP$^s$ release is "triggered" or signaled by activation of cell-surface neurotransmitter receptors), and that the regulatory effect on the release of APP$^s$ derivatives is receptor-subtype specific (i.e., is controlled or signaled by activation of cell-surface neurotransmitter receptors which are linked to phospholipase C and a protein kinase, such as protein kinase C (PKC)). This work has resulted in the description of a novel cell-surface neurotransmitter receptor-mediated mechanism for the stimulation of release of soluble NH$_2$-terminal APP derivatives.

Human cells expressing serotonin surface receptors linked to phospholipase C and protein kinase C, e.g. the 5HT$_{1C}$ or 5HT$_2$ subtypes, have been shown to release the water-soluble NH$_2$-terminal cleavage product of APP (APP$^s$) when activated by serotonin. Thus, activation of 5HT$_{1C}$ or 5HT$_2$ receptors results in the stimulation of non-amyloidogenic processing, i.e. the release of the NH$_2$ terminal cleavage product of APP, and the suppression of amyloidogenic processing. Activation of 5HT$_{1C}$ or 5HT$_2$ receptors in an individual can therefore prevent or retard the formation of amyloid plaques associated with Alzheimer's Disease. A method comprising activating cells expressing 5HT$_{1C}$ or 5HT$_2$ subtypes in vitro have utilities such as identifying new agents which stimulate non-amyloidogenic processing and are therefore drug candidates for therapies for Alzheimer's disease.

One embodiment of the present invention is a method of stimulating non-amyloidogenic processing and/or suppressing amyloidogenic processing in a cell by contacting the cell with an agent which causes the activation of the cell surface serotonin receptor which is linked to phospholipase C and a protein kinase. As a result, formation of amyloid in Azheimer's Disease can be prevented, its onset delayed or its severity reduced. The serotonin receptors can be activated directly by a serotonin receptor agonist such as dexnorfenfluramine, which is shown herein to cause the release of APP$^s$ from cells expressing 5HT$_{1C}$ or 5HT$_2$ on their cell surfaces. The serotonin receptors can also be activated by increasing the intrasynaptic and intracellular concentrations of serotonin, for example by inhibiting the re-uptake of serotonin by the cells, by causing release of serotonin at the nerve terminals or by promoting the biosynthesis of serotonin.

Another embodiment of the present invention is a method of stimulating non-amyloidogenic processing and/or suppressing amyloidogenic processing in the brain of an individual by administering a therapeutically effective dose of an agent which causes the activation of cell surface serotonin receptors linked to phospholipase C and protein kinase C. This method prevents amyloid deposition in the individual and can therefore be used as a treatment for an individual with a disease in which amyloid is deposited in the brain (e.g., Alzheimer's Disease).

The present invention also is a method of identifying new agents and optimizing the activity of known agents which stimulate non-amyloidogenic processing and are therefore drug candidates against Alzheimer's disease. In one aspect the method identifies agents which are serotonin receptor agonists or optimizes the activity of serotonin agonists. In another aspect the method identifies new agents which block the reuptake of serotonin from synapses or optimizes the activity of agents which act by this mechanism. In yet another aspect, the method identifies new agents which cause the release of serotonin from nerve cells or optimizes the activity of agents which act by this mechanism.

DETAILED DESCRIPTION OF THE INVENTION

Figure 1A:
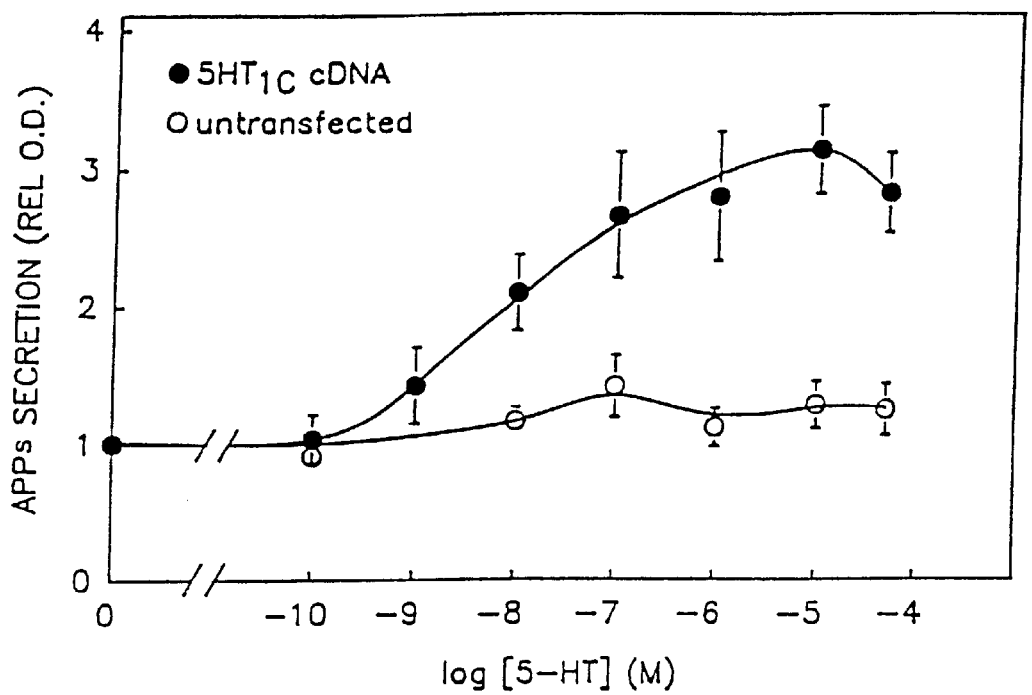
FIGS. 1A, 1B, 1C and 1D are graphic representations of time (1B and 1D) and concentration (1A and 1C) dependent APP$^S$ release by NIH 3T3 cells transfected with and expressing the genes for the human serotonin-1C (1A and 1B) or serotonin-2 (1C and 1D) surface receptors in response to activation by serotonin. For the time courses, the serotonin concentration was 10 µM. The inset in FIG. 1C is a graphic representation of the ability of serotonin receptor antagonists to block serotonin APP$^S$ release from NIH 3T3 cells expressing 5HT$_2$ on their surface.

The present invention is based on a discovery relating to the stimulation of APP processing. As described herein, non-amyloidogenic APP processing, which produces water-soluble proteolytic cleavage products which lack the COOH terminal domain of APP, is stimulated by activation of specific subtypes of cell-surface neurotransmitter receptors which are linked to phospholipase C and to a protein kinase, such as protein kinase C (PKC). Suitable cell-surface neurotransmitter receptors include muscarinic receptors, bradykinin receptors and serotonin receptors. In particular, the present invention refers to stimulating APP processing by activating serotonin-1C or serotonin-2 receptors.

As used herein, "stimulating non-amyloidogenic processing" refers to enhancing the breakdown of APP to water soluble NH$_2$-terminal APP fragments as a result of cleavage within the β/A4 domain of APP. "Suppressing amyloidogenic processing" refers to slowing or inhibiting the breakdown of APP into the 39–42 amino acid β/A4 peptide found in the amyloid deposits which are characteristic of Alzheimer's disease. Suppressing amyloidogenic APP processing and stimulating non-amyloidogenic processing have the same or similar results, namely the suppression of or reduction in the formation of amyloid plaques, neurofibrillary tangles and the neuronal degeneration associated with Alzheimer's Disease.

The present invention is based on the discovery that when serotonin activates serotonin-1C or serotonin-2 receptors, non-amyloidogenic processing (i.e. the cleavage of APP to the soluble NH$_2$-terminal cleavage product) is enhanced. Cultured NIH 3T3 cells, when stably transfected with cDNA expression constructs for the serotonin-1C or serotonin-2 receptor both express the respective receptor and show an increase in APP secretion in the presence of serotonin or a serotonin receptor agonist (see FIG. 1 and the Example). Serotonin receptor antagonists, such as ketanserin, mianserin and ritanserin, abolish the ability of serotonin to stimulate non-amyloidogenic processing in NIH 3T3 cells expressing 5HT$_2$, indicating that serotonin increases non-amyloidogenic processing by acting at the 5HT$_2$ receptor. Although Applicants do not wish to be bound by any particular mechanism, it is believed that serotonin acts by activating phospholipase C, causing the breakdown of membrane phosphatidylinositol and membrane phosphatidylcholine, liberating diacylglycerol. The enzyme which cleaves APP into the soluble NH$_2$-terminal cleavage product is thereby activated.

These results show that non-amyloidogenic APP processing can be stimulated and amyloidogenic processing can be suppressed by agents which cause the activation of serotonin receptors which are linked to phospholipase C and protein kinase C, such as 5HT$_{1C}$ or 5HT$_2$. These results also suggest that stimulating serotonin receptors that are linked to phospholipase C and protein kinase C in the brain can be useful in treating an individual with a disease such as Alzheimer's Disease in which amyloid deposition occurs in the brain. Stimulating these receptors in the brain of such an individual will decrease the deposition of amyloid by enhancing non-amyloidogenic APP processing and suppressing amyloidogenic APP processing in the brain.

One embodiment of the present invention is a method of stimulating non-amyloidogenic APP processing in a cell having a cell surface serotonin receptor linked to phospholipase C and protein kinase C. Suitable serotonin receptors include serotonin-1C receptors or serotonin-2 receptors. The method comprises contacting the cell with an agent which causes the activation of the cell surface serotonin receptor.

Figure 2A:
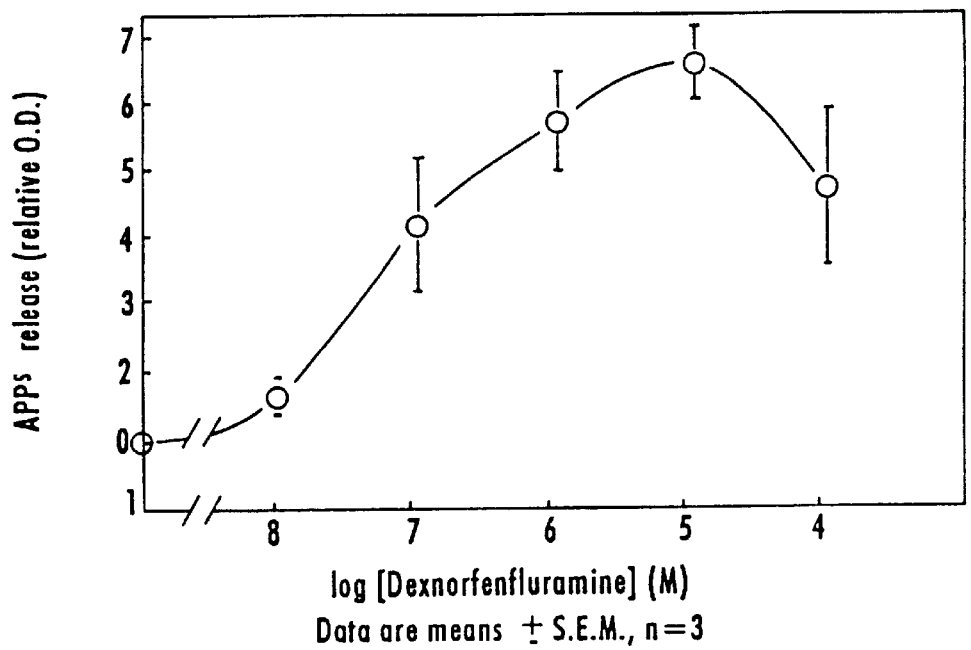
FIG. 2A is a graphic representation of concentration dependent APP$^S$ release by NIH 3T3 cells transfected with and expressing the gene for the human serotonin-1C surface receptor in response to activation by dexnorfenfluramine.
Figure 2B:
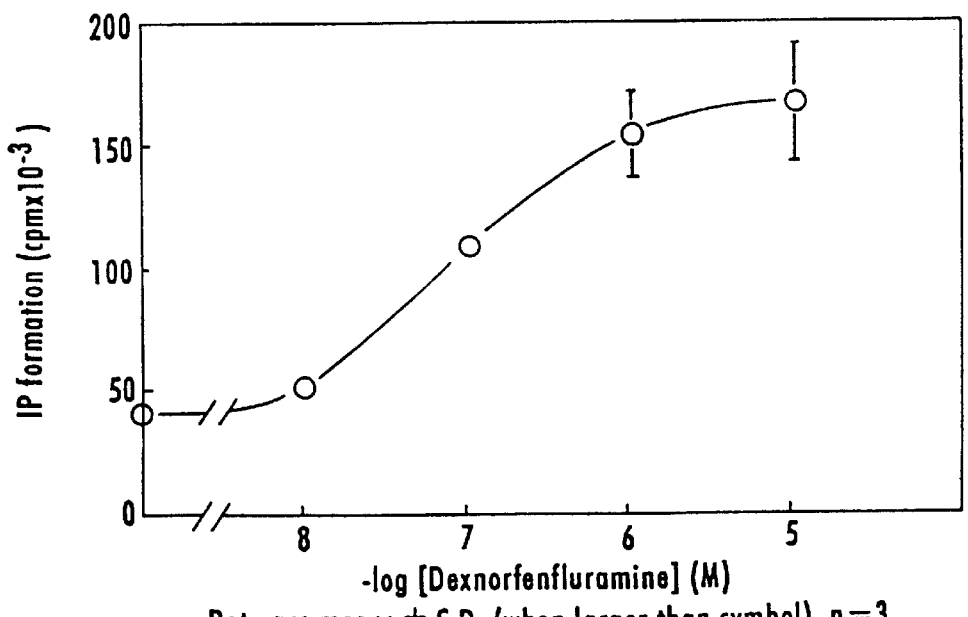
FIG. 2B is a graphic representation of phosphatidylinositol turnover in the same cells in response to activation by dexnorfenfluramine.
Figure 3:
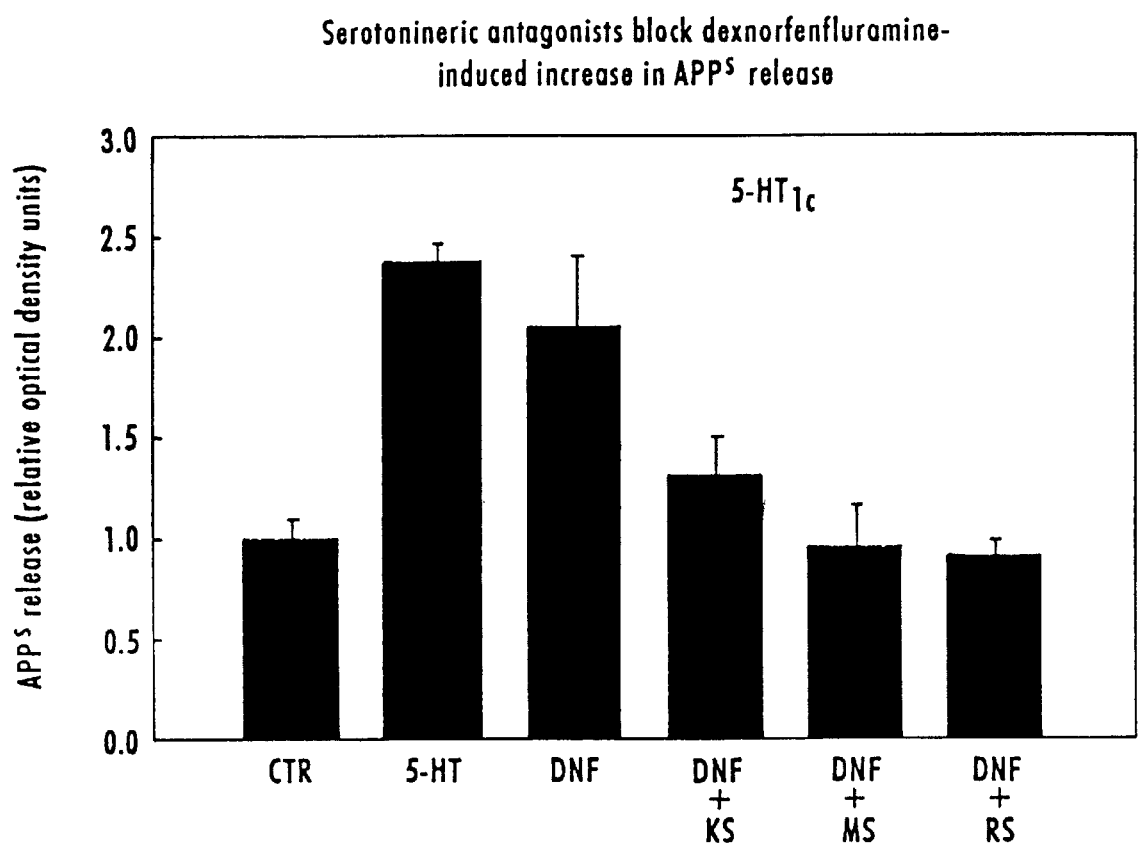
FIG. 3 is a graphic representation of the ability of serotonin receptor antagonists to block nordexfenfluramine induced APP$^S$ release from NIH 3T3 cells expressing 5HT$_{1C}$ on their surface.

Many different agents can cause the activation of a cell surface serotonin receptor linked to phospholipase C and protein kinase C. In one embodiment of the present invention, the agent which causes the activation of these cell surface serotonin receptors is a serotonin receptor agonist. In this instance, the agent interacts with and stimulates the serotonin surface receptor directly. The serotonin receptor agonist is, for example, dexnorfenfluramine ((+) 1-[3-(trifluoromethyl)-phenyl] propan-2-amine hydrochloride), which increases the secretion of the water soluble NH$_2$-terminal APP fragment from cultured NIH 3T3 cells stably transfected with cDNA expression constructs for the serotonin 1-C receptor (see the Example and FIG. 2A). Evidence that dexnorfenfluramine is stimulating the serotonin receptor is provided by the observation that the serotonin receptor antagonists ketanserin, ritanserin and mianserin block dexnorfenfluramine induced release of APP$^S$ from NIH 3T3 cells expressing 5-HT$_{1C}$ on their surfaces (FIG. 3 and the Example). Additional evidence is provided by the observation that turnover of phosphatidylinositol is stimulated in these cells by dexnorfenfluramine (FIG. 2B).

In a further embodiment of the present invention, the agent which causes the activation of a cell surface serotonin receptor which is linked to phospholipase C and a protein kinase is an agent which increases intrasynaptic levels of serotonin. High intrasynaptic concentrations of serotonin will lead to increased stimulation of serotonin-1C or serotonin-2 receptors, thereby leading to increased non-amyloidogenic processing and decreased amyloidogenic processing. Intrasynaptic levels of serotonin can, for example, be increased by agents which cause serotonin to be released directly from the nerve terminal. For example, dexnorfenfluramine, in addition to being a serotonin receptor agonist, also causes serotonin to be released directly from the nerve terminal. A 6–7 fold increase in the release of serotonin results when 100 µM dexnorfenfluramine are incubated in slices of rat brain (R. Samanin and S. Garattini, "The Pharmacology of Serotoninergic Drugs Affecting Appetite," in *Nutrition and the Brain,* Volume 8, pp. 163–192 (1990)). Increases in the serotonin level to a local concentration of about 1 μM to about 20 μM are sufficient to promote non-amyloidogenic APP processing. Other agents which promote serotonin release from nerve terminals include fenfluramine and norfenfluiamine.

Intrasynaptic levels of serotonin can also be increased by preventing or inhibiting the reuptake of serotonin by the cells after release into the synapse. The activation or stimulation of a nerve cell causes the release of neurotransmitters such as serotonin into the synapses. Following the release of neurotransmitter into the synapses, intrasynaptic concentrations of the neurotransmitter are returned to the pre-release levels through the reuptake of the neurotransmitter by the nerve cells. Agents which block the reuptake of serotonin into the nerve cells maintain high extracellular concentrations of serotonin, thereby causing increased activation of serotonin-2C and serotonin-1 receptors and increasing non-amyloidogenic processing. In a preferred embodiment, the reuptake of serotonin from the synapse is blocked by contacting the serotonin-2C or serotonin-1 receptor with dexfenfluramine (R. Samanin and S. Garattini, "The Pharmacology of Serotoninergic Drugs Affecting Appetite," in *Nutrition and the Brain,* Volume 8, pp. 163–192 (1990)). Other agents which inhibit the reuptake of serotonin include fluoxetine, sertraline, paroxetine, and fluvoxamine (R. Samanir. and S. Garattini, "The Pharmacology of Serotoninergic Drugs Affecting Appetite," in *Nutrition and the Brain,* Volume 8, pp. 163–192 (1990)).

The reuptake of serotonin can be inhibited by blocking pre-synaptic receptors for serotonin by causing the pre-synaptic receptor to come in contact with an agent which acts as an antagonist for the serotonin pre-synaptic receptor. Serotonin pre-synaptic receptors differ from the serotonin-2 and serotonin-1C receptors in that activation of the pre-synaptic receptor results in reuptake of serotonin from the synapse while activation of serotonin-1C or serotonin-2 receptors results in the activation of phospholipase C and protein kinases, as described earlier. Activation of the pre-synaptic receptors typically occurs when the intrasynaptic concentration of the neurotranmitter is high. The activation of these presynaptic receptors stimulates the nerve cell to reabsorb the neurotransmitter, thereby causing the extracellular concentration of neurotransmitter to decline. Agents which block the pre-synaptic receptor for serotonin increase amyloidogenic processing and decrease non-amyloidogenic processing by causing the extracellular concentrations of serotonin to remain high.

In addition, neurotransmitters released into the synapses are metabolized by enzymes such as monoamine oxidase. Agents which inhibit monoamine oxidase will similarly maintain high extracellular concentrations of serotonin, thereby increasing non-amyloidogenic processing.

Intrasynaptic levels of serotonin can also be increased by agents which promote the biosynthesis of serotonin. Suitable agents which promote the biosynthesis of serotonin include tryptophan and 5-hydroxytryptophan, which are converted into serotonin in vivo.

Agents which stimulate non-amyloidogenic processing in vitro can be similarly used to stimulate non-amyloidogenic processing in vivo. Non-amyloidogenic processing in the cells of the central nervous system of an animal or individual can be stimulated and amyloidogenic processing inhibited by a method in which the cells of the central nervous system are contacted with an agent which causes the activation of a cell surface serotonin receptor that is linked to phospholipase C and protein kinase C. For example, when dexfenfluramine is taken orally by an individual, roughly equal amounts of this compound and its de-ethylated metabolite, dexnorfenfluramine, appear in the brain of the individual (M. R. Fleisher and S. Campbell, *The Lancet,* 1369: 1306 (1969)). As discussed earlier, dexnorfenfluramine stimulates the release of APP$^S$ in cells expressing $5HT_{1C}$ or $5HT_2$ receptors by acting as an agonist for these receptors and stimulating the release of serotonin while dexfenfluramine activates these receptors by inhibiting the re-uptake of serotonin from the synapse. Consequently, administration of therapeutically effective doses of dexfenfluramine and/or dexnorfenfluramine would be expected to stimulate non-amyloidogenic processing and suppress amyloidogenic processing. Therapeutically effective doses of dexfenfluramine, dexnorfenfluramine or other drug are those doses which result in a sufficient level of $5HT_{1C}$ or $5HT_2$ receptor activation in the brain to stimulate non-amyloidogenic processing and suppress amyloidogenic processing. Therapeutically effective doses of dexfenfluramine and/or nordexfenfluramine range from about 5 mg/day to about 100 mg/day, and preferably from about 20 mg/day to about 40 mg/day.

The method of stimulating non-amyloidogenic processing and suppressing amyloidgenic processing in vivo can therefore be used to prevent or retard the deposition of amyloid in the brain of an individual or animal, thereby serving as an effective treatment for a disease in an individual in which amyloid is deposited in the brain, for example Alzheimer's disease. The agent can be administered to the individual after the individual has begun to show symptoms of the disease in order to alleviate or slow the further progression of the disease. Alternatively, the agent can be administered to the individual before the appearance of symptoms of the disease in order to prevent or slow the onset of the symptoms. The agent can be administered alone, or in conjunction with other serotonergic drugs or with other drugs which can be used to treat Alzheimer's disease, e.g., tacrine or physostigmine.

In the method of stimulating non-amyloidogenic processing or inhibiting amyloidogenic processing in an individual, a therapeutically effective dose of the agent is administered to the animal or individual in a manner such that the agent comes in contact with the cells of the central nervous system. The agent can be administered orally, by subcutaneous or other injection, intravenously, parenterally, transdermally, rectally or via an implanted reservoir. The form in which the agent will be administered (e.g., powder, tablet, capsule, solution, emulsion) will depend on the route by which it is administered. The quantity of the agent to be administered will be determined on an individual basis, and will be based at least in part on consideration of the individual's health, age, size and severity of the condition. The agent can be administered with other components; the components included in a particular composition are determined primarily by the manner in which the composition is to be administered. For example, a composition to be administered orally in tablet form can include, in addition to the agent, a filler (e.g., lactose), a binder (e.g., carboxymethyl cellulose, gum arabic, gelatin), an adjuvant, a flavoring agent, a coloring agent and a coating material (e.g., wax or a plasticizer). A composition to be administered in liquid form can include the agent and, optionally, an emulsifying agent, a flavoring agent, and/or a coloring agent. The composition can be administered as a single dose, in multiple doses, or in a form that results in continuous release.

The method of stimulating non-amyloidogenic APP processing in a cell having a cell surface serotonin receptor linked to phospholipase C or a protein kinase by contacting the cell with an agent which causes the activation of the cell surface serotonin receptor has uses in vitro. For example, the method can be used in vitro to identify new agents which cause the activation of these serotonin receptors. These newly identified agents are drug candidates for the treatment of Alzheimer's disease. The method of stimulating non-amyloidogenic processing in vitro can also be used, as described below, in the process of optimizing certain desirable properties (e.g., activity, resistance to biodegradability or lipophilicity) of drug candidates which stimulate non-amyloidogenic processing by activating the serotonin receptors.

The skilled artisan is able to prepare analogs of agents such as dexnorfenfluramine and dexfenfluramine which cause the activation of serotonin receptors linked to phospholipase C and protein kinase C so as optimize desirable properties of the agents. Such analogs can be prepared by techniques standard in the art of organic chemistry. Desirable properties which can be designed into these analogs include optimizing its activity (e.g., its ability to act as a $5HT_{1C}$ or $5HT_2$ agonist), solubility, ability to reach the target site in the brain and ability to avoid degradation within the body. Methods of optimizing these and other properties are well known within the art. For example, increasing the ability of the agent to cross the blood brain barrier and reach the target site can be accomplished by increasing the lipophilicity of the agent. Alternatively, the agent can be modified to include a component that is recognized by a receptor on the blood-brain barrier and allows the agent to be internalized (brought across the blood-brain barrier).

Optimizing activity, i.e., the ability to stimulate non-amyloidogenic processing by activating $5HT_{1C}$ or $5HT_2$ receptors, can be accomplished, for example, by synthesizing analogs of dexnorfenfluramine and comparing the ability of the analog to stimulate non-amyloidogenic processing compared with dexnorfenfluramine. Analogs of $5HT_{1C}$ or $5HT_2$ agonists, wherein the analog has been modified to optimize other desirable properties of the agonist, e.g. the ability to resist degradation in the body, can be similarly tested to determine whether modification of the parent drug has caused a decrease in activity. Thus, the method of stimulating non-amyloidogenic APP processing in vitro by causing the activation of serotonin receptors linked to phospholipase C and protein kinase C is useful for optimizing the activity and other desirable properties of agents which suppress amyloidogenic processing. The activity of agents can be optimized by exposing cells with $5HT_{1C}$ or $5HT_2$ receptors to analogs of the agent and measuring the amount of breakdown products of phosphatidylinositol and comparing to the amount of breakdown product induced by the agent or other suitable control such as serotonin or dexnorfenfluramine. Increased breakdown of phosphatidylinositol caused by the analog of the agent compared with the agent indicates that the analog has increased activity compared with the agent. The amount of $APP^S$ released by cells expressing $5HT_{1C}$ or $5HT_2$ is also indicative of whether activity has been optimized. $APP^S$ release car be quantitated by SDS-polyacrylamide gel electrophoresis and densitometric analysis of Western blots performed with monoclonal antibody 22C11, as described in the Example. (See also "Current Protocols in Molecular Biology," edited by Ausubel et al., (John Wiley and Sons, 1994) and S. Brook, et al., "Molecular Cloning," (Cold Spring Harbor Laboratory Press, 1981). Greater release of $APP^S$ caused by the analog of the agent compared with the agent indicates that the analog is more active than the agent. Non-amyloidogenic products can be distinguished from amyloidogenic products with a polyclonal antiserum against the COOH terminus, as described in the Example.

The activity of agents which block the ability of nerve cells to take up serotonin from the synapses can be optimized by synthesizing analogs of agents which block the reuptake of serotonin from synapses, for example analogs of dexfenfluramine. The ability of these analogs to block the uptake of serotonin by brain or brain synaptosomes compared with dexfenfluramine is then determined. The quantity of serotonin uptake can be determined by measuring the radioactivity in brain slices or brain synaptosomes incubated with radioactive serotonin in the presence of dexfenfluramine or the analog. Less uptake of radioactivity in the presence of the analog compared with dexfenfluramine indicates that the analog is more active than dexfenifluramine. New agents which inhibit the uptake of serotonin can be identified by determining whether less radioactive serotonin is absorbed in the presence of the drug candidate than in its absence. Less radioactivity absorbed by the brain slice or synaptosomes indicates that the drug candidate inhibits the uptake of serotonin. Analogs of agents which inhibit uptake of serotonin wherein the agent has been modified to optimize other desirable properties of the agent, e.g., the ability to resist degradation in the body, can be similarly tested to determine whether the modification has caused a decrease in activity.

The activity of agents which cause the release of serotonin from nerve terminals, for example dexnorfenfluramine, can be optimized by synthesizing analogs of these agents. The ability of these analogs to cause the release of serotonin from nerve terminals is then compared with dexnorfenfluramine. This can be determined by comparing the ability of the analog and dexnorfenfluramine to release radioactivity from brain slices or synaptosomes that have absorbed radioactive serotonin, as described above. A higher release of radioactivity induced by the analog compared with dexnorfenfluramine indicates that the analog is more effective at causing the release of serotonin than dexnorfenfluramine. In addition, new agents which cause the release of serotonin from nerve terminals can be identified by incubating the brain slices or synaptosomes which have absorbed radioactive serotonin with a drug candidate. The release of more radioactivity in the presence of the drug candidate than in its absence indicates hat the drug candidate causes the release of serotonin. Analogs of agents which cause the release of serotonin from the nerve terminal wherein the agent has been modified to optimize other desirable properties of the agent, e.g., the ability to resist degradation in the body, can be similarly tested to determine whether the modification has caused a decrease in activity.

The process of optimizing activity can be aided by rational based drug design, for example by determining an x-ray crystal structure of a complex between dexnorfenfluramine and $5HT_{1C}$ or $5HT_2$ and identifying the significant interactions between the two molecules.

Optimizing the ability of the agent to avoid degradation within the body can be done by metabolic studies in animals, for example by injecting analogs labeled with radioactive isotopes and following their metabolic fate.

The invention is illustrated by the following examples, which are not to be construed as limiting in any way.

EXAMPLE
Regulation of APP Processing by Muscarinic Receptor Subtypes

A. Transection and Growth of 293 Cell Lines

Cultured human NIH 3T3 fibroblasts were utilized. The 3T3 cells were transfected with the genes for human brain serotonin $5HT_{1C}$ and $5HT_2$ receptors well as for neomycin resistance as described (E. G. Peralta, A. Ashkenazi, J. W. Winslow, J. Ramachandran, D. J. Capon, *Nature*, 334: 434 (1988)). Cells were grown in DMEM/F-12 medium containing 10% fetal bovine serum (Gibco) in the presence of the neomycin analog G-418 (0.5 mg/ml) (Geneticin, Gibco). As a control, nontransfected human 3T3 cells were maintained in the absence of G-418.

B. Stimulation and Inhibition of the Serotonin Receptors

Confluent cell cultures on poly-D-lysine-coated ($M_r$ >300,000; 0.1 mg/dish) culture dishes were washed with serum-free N-2 medium (Gibco) and incubated for twenty-four hours in serum-free N-2. Assays were then preformed with or without 10 $\mu$M serotonin (Sigma) and 10 nM–10 $\mu$M dexnorfenfluramine (Servier, France) in the absence of G-418. Conditioned media were centrifuged at 10,000×g (4° C., 5 minutes), desalted on SEPHADEX G-25 columns (Pharmacia) with water as eluent, lyophilized, and reconstituted typically in 150 $\mu$l SDS loading buffer. Total cell protein per dish was measured with the bicinchoninic acid assay (Pierce). Cell proteins were not altered by any of the above treatments.

Figure 1B:
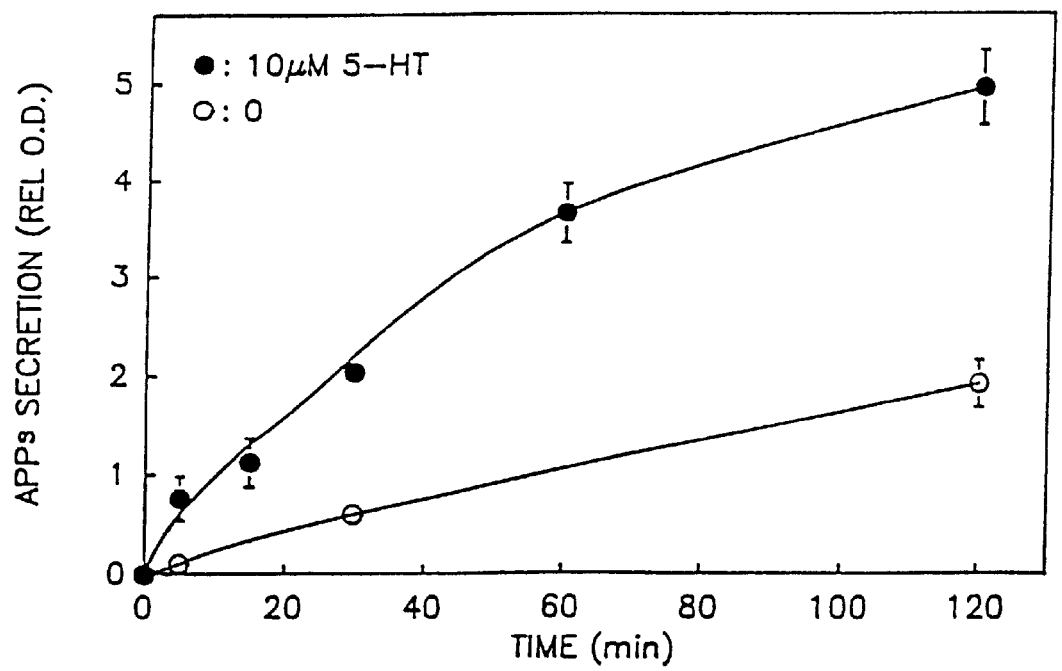

The results indicated that activation by serotonin in cells expressing the genes for the serotonin-1C or serotonin-2 receptors potently stimulated the release of water-soluble APP fragments into the cell culture media. The effect of both serotonin-1C and serotonin-2 stimulation on APP release was rapid: half-maximal stimulation was reached within 30–40 minutes, and the maximum was attained within 120 minutes (FIGS. 1B and 1D). These time-course experiments strongly suggest that preexisting cellular APP was processed in response to receptor activation. Using pulse-chase methods, Weidemann, et al. (A. Weidemann, et al., *Cell*, 57: 115 (1989), M. R. Palmert et al., *Proc. Natl. Acad. Sci. USA*, 86: 6338 (1989)) showed that secreted forms of APP do not appear in the medium until 45 minutes after labelling.

Stimulation of $APP^S$ release by serotonin and dexnorfenfluramine also showed a clear dose-response relationship (FIGS. 1A and 1C for serotonin and 2A and 2B for dexnorfenfluramine) and the $EC_{50}$ values of 5 nM for the $5HT_{1C}$ and 20 nM for the $5HT_2$ transfected cells were virtually identical to those obtained for receptor-coupled phosphatidlinositol turnover in the same cells.

Figure 1C:
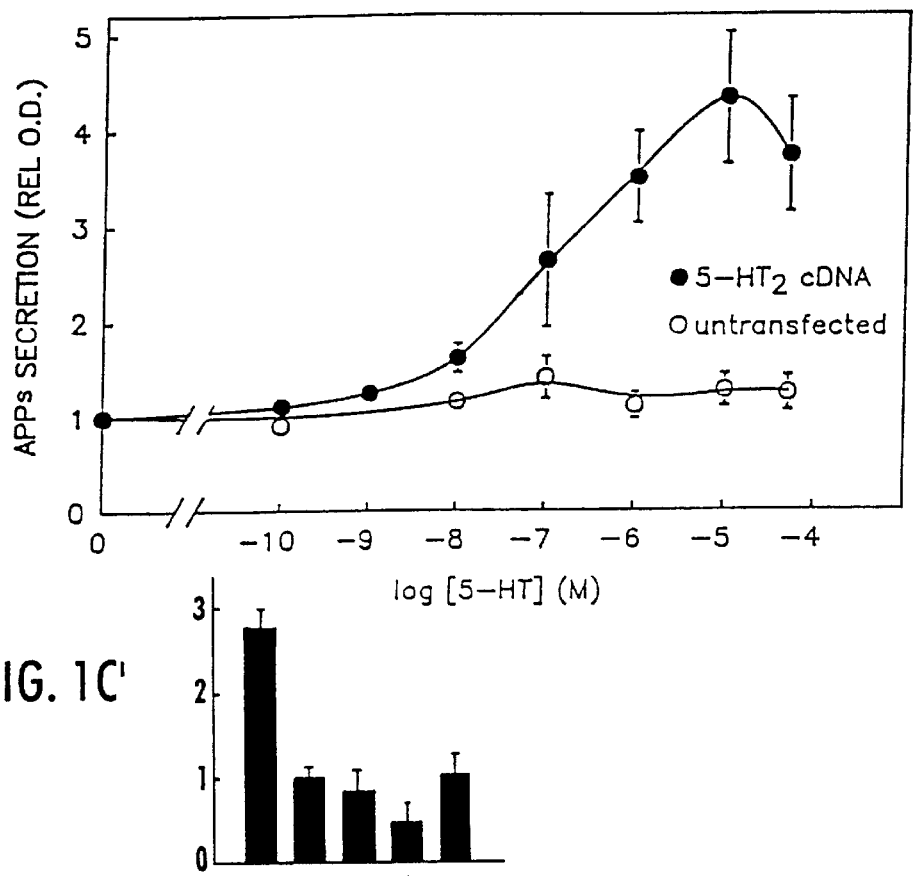
Figure 1C:
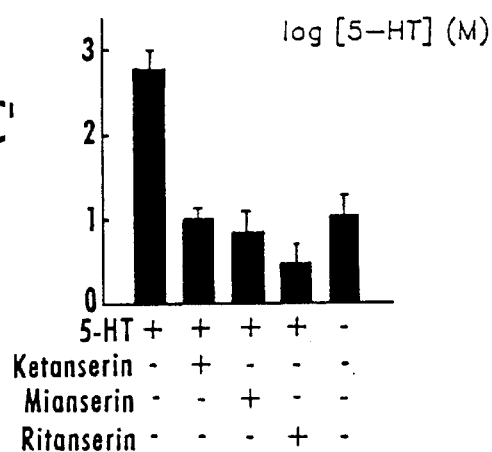
Figure 1D:
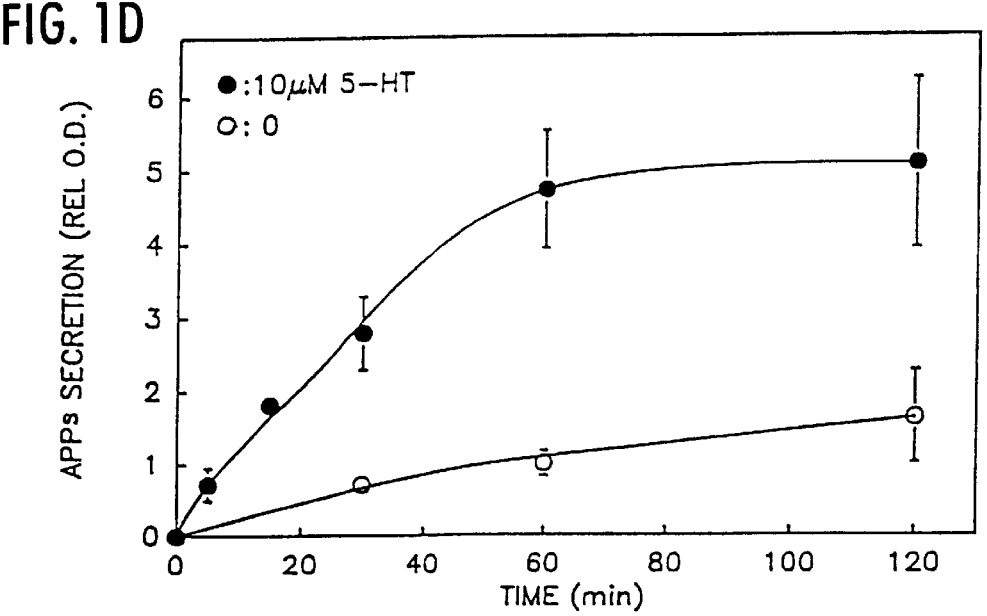

Receptor-activated APP release by $5HT_2$ transfected cell lines in response to serotonin and $5HT_{1C}$ transfected cell lines in response to dexnorfenfluramine was blocked by the serotonin receptor antagonists ketanserin, ritanserin and mianserin, indicating a specific agonist-receptor interaction (see insert in FIG. 1C and FIG. 3). The effect of serotonin was also inhibited by staurosporine, suggesting phosphorylation, presumably by protein kinase C (PKC) activation. Stimulation of serotonin $5HT_{1C}$ or $5HT_2$ receptors activates PKC via diacylglycerol formation (M.J. Berridege and R.F. Irvine, *Nature* 341: 197 (1989)), which, along with inositol phosphate, is a product of phosphatidylinositol hydrolysis (E. G. Peralta, A. Ashkenazi, J. W. Winslow, J. Ramachandran, D. J. Capon, *Nature*, 334: 434 (1988); J. Sandmann, E. G. Peralta, R. J. Wurtman, *J. Biol. Chem.* 266: 6031 (1991)). Receptor-coupled APP release may thus be mediated by diacylglycerol-induced PKC activation, or by an interaction of diacylglycerol and calcium released from internal pools by inositol triphosphate (M. J. Berridge, R. F. Irvine, *Nature* 341: 197 (1989)). Downregulation of PKC by chronic treatment with phorbol esters did not block the effect of serotonin, suggesting redundant signal transduction pathways that couple receptor activation to $APP^S$ secretion. PKC activation by phorbol esters has been previously shown to increase both the release of $NH_2$-terminal APP fragments as well as the abundance of cell-associated COOH-terminal APP cleavage products in PC-12 cells, and to phosphorylate APP at $Ser^{655}$ in semi-intact PC-12 cells (G. L. Caparaso, S. E. Gandy, J. D. Buxbaum, T. V. Ramabhadran, P. Greengard, *Proc. Natl. Acad. Sci. U.S.A.*, 89: 3055 (1992); Buxbaum, et al., *Proc. Natl. Acad. Sci. U.S.A.*, 87: 6003 (1990); T. Suzuki, A. C. Nairn, S. E. Gandy, P. Greengard, Neurosci. 48: 755 (1992)). Although a causal relationship between phosphorylation of APP and its cleavage has not yet been established, purified PKC can directly phosphorylate a synthetic COOH-terminal APP fragment (S. Gandy, A. J. Czernik, P. Greengard, *Proc. Natl. Acad. Sci. U.S.A.* 85: 6218 (1988)). It is also possible that other receptor species linked to phosphatidylinositol turnover, and thus to receptor-coupled generation of diacylglycerol with subsequent activation of PKC, may also regulate APP release. APP release was not stimulated by increased intracellular calcium levels alone, as indicated by the failure of the calcium ionophore A23187 to mimic the receptor-mediated stimulation of basal APP release.

C. Analysis of the APP Fragments Released

Reconstituted culture media proteins corresponding to 150 $\mu$g of total cell protein were separated by SDS-polyacrylamide gel electrophoresis on 12% gels and Western blots were performed with the monoclonal antibody 22C11 directed against a purified full-length APP fusion protein (A. Weidemann, et al., *Cell*, 57: 115 (1989), M. R. Palmert, et al., *Proc. Natl. Acad. Sci. USA*, 86: 6338 (1989)). Molecular weight standards were obtained from Amersham. Cells were lysed on ice in a buffer containing 2% TRITON X-100, 2% SDS, 0.1 M Tris (pH 6.8), 15% glycerol, EDTA (5 mM), phenylraethylsulfonyl fluoride (2 mM), aprotinin (10 $\mu$M), leupeptin (1 $\mu$g.ml), pepstatin (0.1 $\mu$g/ml), and Tosyl-L-lysine chloromethyl ketone (1 $\mu$g,ml), (all from Sigma), ultrasonicated, boiled (5 minutes), and diluted 1:1 in SDS-free loading buffer. Equal amounts of cell protein (20 $\mu$g/lane) and media corresponding to 300 $\mu$g of total cell protein were separated on 7.5% SDS-polyacrylamide gels, and Western blots performed as described (A.

Weidemann, et al., *Cell*, 57: 115 (1989), M. R. Palmert, et al., *Proc. Natl. Acad. Sci. USA*, 86: 6338 (1989)). For each treatment group represented on the Western blots, proteins secreted into the conditioned media and cell-associated proteins were obtained from the identical culture dishes.

The immunoreactive bands were compared densitometrically using a LKB Ultroscan laser scanner. Scanning parameters included 40 $\mu$m vertical scanning intervals at a total slit width of 2.4 mm (3×0.8 mm), and automatic subtraction of the absorbance offset determined for each blot individually. Measurements were performed in the linear range which was determined using dilution curves of cell protein extracts. Results were normalized to basal APP release from vehicle-treated controls determined within the same blot. Experiments were done with duplicate or triplicate cell culture dishes and repeated 5 to 7 times for statistical analysis with Mann-whitney rank sum tests or analysis of variance and post hoc Scheffe tests as indicated.

The densitometric analysis indicated that receptor activation with serotonin increased the basal APP release 3-fold (FIG. 1C) in the $5HT_2$ transfected cells, and 4-fold in the 5HT$_{1C}$ transfected cells (FIG. 1A). Dexnorfenfluramine stimulated APP$^S$ secretion 3-fold. These results show that cellular APP release can be controlled by cell-surface neurotransmitter activity. Basal release of APP fragments from wild-type cell lines was not stimulated by serotonir (FIGS. 1A and 1C).

The results of the blots showed that stimulation with serotonin decreased the abundance of cell-associated 141 kD APP, whereas the cell-associated 115 kD APP remained unaffected. The concomitant serotonin-induced increase of a 128 kD APP derivative secreted into the culture medium suggests that the secreted 128 kD protein is a cleavage product of the cell-associated 141 kD APP.

In order to investigate whether the secreted APP fragments were cleavage products of the parent protein lacking the COOH terminus, a polyclonal antiserum against the COOH terminus was used (D. J. Selkoe, et al., *Proc. Natl. Acad. Sci. USA*, 85: 7341 (1988)). Western blot analysis of cell-associated APP in both 5HT$_{1C}$ and 5HT$_2$ cell lines using this antiserum revealed the expected pattern of APP and APP fragments which was similar to that described in human brain cortex (D. J. Selkoe, et al., *Proc. Natl. Acad. Sci. USA*, 85: 7341 (1988)). This antiserum did not detect any APP fragments in conditioned media obtained from stimulated or unstimulated 5HT$_{1C}$ and 5HT$_2$ transfected cell lines, indicating that the secreted APP fragments are indeed APP cleavage products lacking the COOH terminus.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of preventing, delaying or reducing the formation of amyloid plaques deposited in the brain of an individual in need thereof comprising administering to said individual a therapeutically effective amount of an agent selected from the group consisting of dexnorfenfluramine, dexfenfluramine, fenfluramine, fluoxetine, sertraline, paroxetine, fluvoxamine, tryptophan and 5-hydroxytryptophan.

2. A method of preventing, delaying or reducing the formation of amyloid plaques associated with a disease in which amyloid is deposited in the brain of an individual, by decreasing amyloidogenic APP processing in cells of the central nervous system of the individual, comprising administering to the individual in need thereof, a therapeutically effective dose of an agent selected from the group consisting of: dexnorfenfluramine, dexfenfluramine, fenfluramine, fluoxetine, sertraline, paroxetine, fluvoxamine, tryptophan and 5-hydroxytryptophan, wherein the agent is administered to the individual in such a manner that the agent contacts cells in the central nervous system.

3. A method of preventing, delaying or reducing the formation of amyloid plagues associated with a disease in which amyloid is deposited in the brain of an individual, comprising administering to the individual in need thereof, a therapeutically effective dose of an agent selected from the group consisting of: dexnorfenfluramine, dexfenfluramine, fenfluramine, fluoxetine, sertraline, paroxetine, fluvoxamine, tryptophan and 5-hydroxytryptophan, wherein the agent is administered to the individual in such a manner that the agent contacts cells in the brain which have the cell surface serotonin receptor.

4. A method of treating Alzheimer's disease in an individual in which amyloid is deposited in the brain, comprising administering to the individual a therapeutically effective dose of an agent selected from the group consisting of: dexnorfenfluramine, dexfenfluramine, fenfluramine, fluoxetine, sertraline, paroxetine, fluvoxamine, tryptophan and 5-hydroxytryptophan, in such a manner that the agent contacts cells in the brain which have the cell surface serotonin receptor.

5. The method of claim 4 additionally comprising administering to the individual a drug used in the treatment of Alzheimer's Disease.

6. A method of treating an individual who has Alzheimer's disease in which amyloid is deposited in the brain, comprising administering to the individual a therapeutically effective dose of dexnorfenfluramine.

7. The method of claim 6, additionally comprising administering to the individual a drug used in the treatment of Alzheimer's Disease.

8. The method of claim 1, said individual suffers from Alzheimer's disease.

9. The method of claim 2, wherein the disease in which amyloid is deposited in the brain is Alzheimer's disease.

10. The method of claim 3, wherein the disease in which amyloid is deposited in the brain is Alzheimer's disease.

11. A method of alleviating or delaying the progression of Alzheimer's disease in which amyloid is deposited in the brain of an individual in need thereof, comprising administering to the individual a therapeutically effective amount of an agent selected from the group consisting of:

dexnorfenfluramine, dexfenfluramine, fenfluramine, fluoxetine, sertraline, paroxetine, fluvoxamine, tryptophan and 5-hydroxytryptophan.

12. The method of claim 11, additionally comprising administering to the individual a drug used in the treatment of Alzheimer's Disease.

13. A method of treating Alzheimer's disease in an individual in need thereof comprising administering to said individual a therapeutically effective amount of an agent selected from the group consisting of dexnorfenfluramine, dexfenfluramine, fenfluramine, fluoxetine, sertraline, paroxetine, fluvoxamine, tryptophan and 5-hydroxytryptophan.

14. The method according to claim 13, wherein said agent is dexnorfenfluramine.

15. The method according to claim 13, wherein said agent is dexfenfluramine.

16. The method according to claim 13, wherein said agent is fluoxetine.

17. The method according to claim 13, wherein said agent is sertraline.

18. The method according to claim 13, wherein said agent is paroxetine.

19. The method according to claim 13, wherein said agent is fluvoxamine.

20. The method according to claim 13, wherein said agent is tryptophan.

21. The method according to claim 13, wherein said agent is 5-hydroxytryptophan.

22. The method according to claim 1, wherein said agent is dexnorfenfluramine.

23. The method according to claim 1, wherein said agent is dexfenfluramine.

24. The method according to claim 1, wherein said agent is fluoxetine.

25. The method according to claim 1, wherein said agent is sertraline.

26. The method according to claim 1, wherein said agent is paroxetine.

27. The method according to claim 1, wherein said agent is fluvoxamine.

28. The method according to claim 1, wherein said agent is tryptophan.

29. The method according to claim 1, wherein said agent is 5-hydroxytryptophan.

* * * * *